(12) United States Patent
Shin et al.

(10) Patent No.: US 8,591,569 B2
(45) Date of Patent: Nov. 26, 2013

(54) STENT FOR PROSTATIC URETHRA EXPANSION

(75) Inventors: Kyong-Min Shin, Seoul (KR);
Jeung-Hee Nam, Kyunggi-do (KR);
Kang-Sun Hong, Seoul (KR);
Ho-Young Song, Seoul (KR);
Tae-Hyung Kim, Seoul (KR)

(73) Assignees: TAEWOONG MEDICAL Co., Ltd., Gyeonggi-do (KR); Kyong-Min Shin, Seoul (KR); Ho-Young Song, Seoul (KR)

( * ) Notice: Subject to any disclaimer, the term of this patent is extended or adjusted under 35 U.S.C. 154(b) by 162 days.

(21) Appl. No.: 12/892,586

(22) Filed: Sep. 28, 2010

(65) Prior Publication Data
US 2011/0098825 A1    Apr. 28, 2011

(30) Foreign Application Priority Data
Oct. 27, 2009    (KR) .................... 10-2009-0102298

(51) Int. Cl.
*A61F 2/06*    (2013.01)
*A61F 2/04*    (2013.01)
*A61B 17/08*   (2006.01)

(52) U.S. Cl.
USPC ....... 623/1.14; 623/1.11; 623/1.15; 623/1.36; 623/23.66; 606/157

(58) Field of Classification Search
USPC ............. 623/23.64, 23.66, 23.67, 23.7, 1.13, 623/1.14, 1.15, 1.18, 1.2, 1.36, 1.35; 606/228
See application file for complete search history.

(56) References Cited

U.S. PATENT DOCUMENTS

| | | | | |
|---|---|---|---|---|
| 6,004,347 | A  * | 12/1999 | McNamara et al. | 623/23.64 |
| 6,231,581 | B1 * | 5/2001  | Shank et al.    | 606/157   |
| 7,081,132 | B2 * | 7/2006  | Cook et al.     | 623/1.36  |
| 2011/0071613 | A1 * | 3/2011 | Wood et al.    | 623/1.11  |

* cited by examiner

*Primary Examiner* — David Isabella
*Assistant Examiner* — Yashita Sharma
(74) *Attorney, Agent, or Firm* — IP & T Group LLP

(57) ABSTRACT

Disclosed herein is a stent for prostatic urethra expansion which does not generate bladder stones, is removable without causing injury on a urethra, and does not generate atrophy of a prostatic urethra even after removal. The stent for prostatic urethra expansion include a stent unit including a cylindrical body with space parts formed by knotting or crossing shape memory alloy wires and bending terminals formed at both ends of the cylindrical body, a pair of hook wires passing through the space parts and knotted to the shape memory alloy wires, both ends thereof being wound on the bending terminals and then being bent upwardly to produce hooks, and a pair of hanging strings arranged in opposite directions to form a hanging knot. The stent for prostatic urethra expansion does not move into the bladder, and expands and maintains a lumen of the stenosed prostatic urethra, thereby reducing post-operative recovery time.

7 Claims, 11 Drawing Sheets

STENT FOR PROSTATIC URETHRA EXPANSION

CROSS-REFERENCE TO RELATED APPLICATION

The Present Application claims priority of Korean Patent Application No. 10-2009-0102298, filed on Oct. 27, 2009, which is incorporated herein by reference in its entirety.

BACKGROUND OF THE INVENTION

1. Field of the Invention

The present invention relates to a stent for prostatic urethra expansion, and more particularly to a stent for prostatic urethra expansion which does not generate bladder stones, is removable without causing injury on a urethra, and does not generate atrophy of a prostatic urethra even after removal.

2. Description of the Related Art

In the past, prostatism was generally defined as an enlarged prostate which gets fat, blocks a discharge passage of urine under a bladder, and thus causes urethral obstruction to reduce a urine flow.

However, histologically, prostatism is defined as proliferation of stromal cells or epithelial cells of the prostate.

That is, the pathology of prostatism is very complicated now, and thus prostatism is difficult to describe with the above definition or concept. At present, prostatism is defined as lower urinary tract symptoms including bladder storage symptoms, such as pollakiuria representing a state that a male who is 50 years old or more abnormally frequently discharges urine more than 8 times or more a day, nycturia, and urgency representing a state of being incapable of holding urine while having strong and sudden desire to urinate, and bladder dysfunctions, such as delay (a state of discharging urine after a designated time), interruption (a state of interrupting a urine flow), and pushing during urination.

Such prostatism is treated with aerotherapeutics and pharmacotherapy. However, pharmacotherapy requires a considerably long time, and pain due to prostatism continues to occur during treatment using pharmacotherapy.

Accordingly, a treatment for prostatism which eliminates the sensation that urine remains even after urination and facilitates smooth urination has been desperately required.

SUMMARY OF THE INVENTION

Therefore, the present invention has been made in view of the above problems, and it is an object of the present invention to provide a stent for prostatic urethra expansion which does not generate stones, does not move to the inside of a bladder, and expands and maintains a lumen of a stenosed prostatic urethra.

It is another object of the present invention to provide a stent for prostatic urethra expansion in which a membrane is fastened to the external surface of a stent unit so as to prevent luminal tissues of a prostatic urethra from being stenosed to the stent unit.

It is a further object of the present invention to provide a stent for prostatic urethra expansion in which a hanging direction of the hooks is reverse to a removing direction of the stent so as to prevent injury of the stent on a lumen of a prostatic urethra during removal of the stent from the prostatic urethra.

In accordance with the present invention, the above and other objects can be accomplished by the provision of a stent for prostatic urethra expansion to expand and maintain a lumen of an organ of a human body stenosed due to lesion, including a stent unit including a cylindrical body provided with space parts formed by knotting or crossing, in a zigzag shape, one or more strands of shape memory alloy wires, and a plurality of bending terminals formed at both ends of the cylindrical body along the circumference of the cylindrical body, a pair of hook wires passing through the plural space parts located in the lengthwise direction of the cylindrical body and knotted to the shape memory alloy wires so as to cross each other in a zigzag shape, both ends of the hook wires being wound on the bending terminals opposite to each other in the circumferential direction of the cylindrical body and then being bent upwardly to the outside to produce hooks, and a pair of hanging strings arranged in opposite directions such that the hanging strings pass through the space parts of one end of the cylindrical body at which the hooks are formed, are hung onto the bending terminals, and are knotted together so as to form a hanging knot located at the center of the cylindrical body, wherein the stent for prostatic urethra expansion is inserted into a prostatic urethra such that the hooks are hung on the inner wall of a lumen of the prostatic urethra to prevent the stent unit from moving to a bladder, expands the lumen of the prostatic urethra narrowed due to prostatism or prostate cancer, and then is removed from the prostatic urethra through release of the hooks from the inner wall of the lumen of the prostatic urethra due to a reduced volume of the stent unit by pulling the hanging knot.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, preferred embodiments of the present invention will be described in detail with reference to the accompanying drawings.

Figure 1:
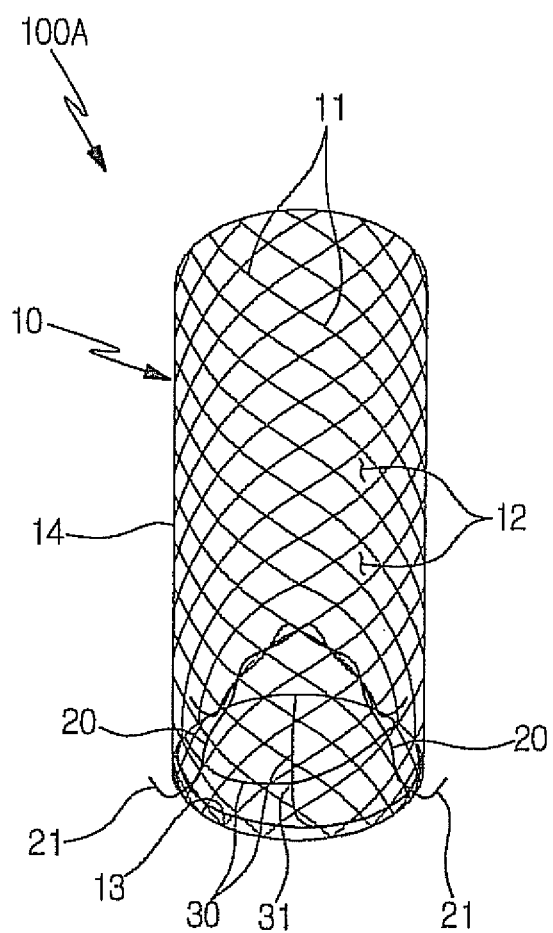
FIG. 1 is a perspective view of a stent for prostatic urethra expansion in accordance with the present invention.
Figure 2:
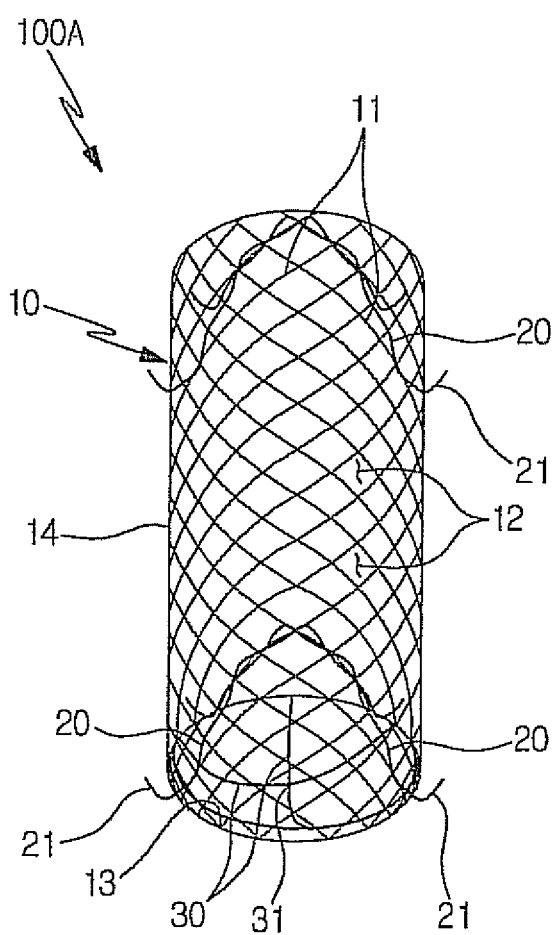
FIG. 2 is a perspective view of the stent for prostatic urethra expansion of FIG. 1, in which hooks are formed at upper and lower portions of a stent unit.
Figure 3A:
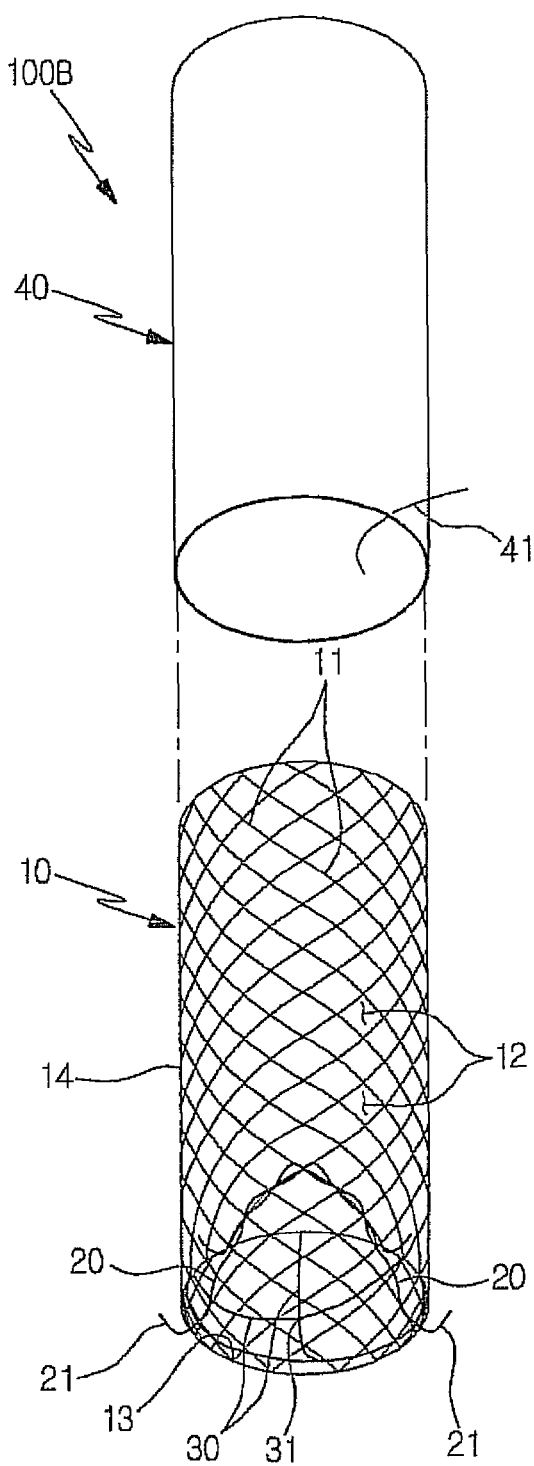
FIGS. 3A and 3B are exploded and assembled perspective views of the stent unit of FIG. 1 and a membrane, respectively.
Figure 3B:
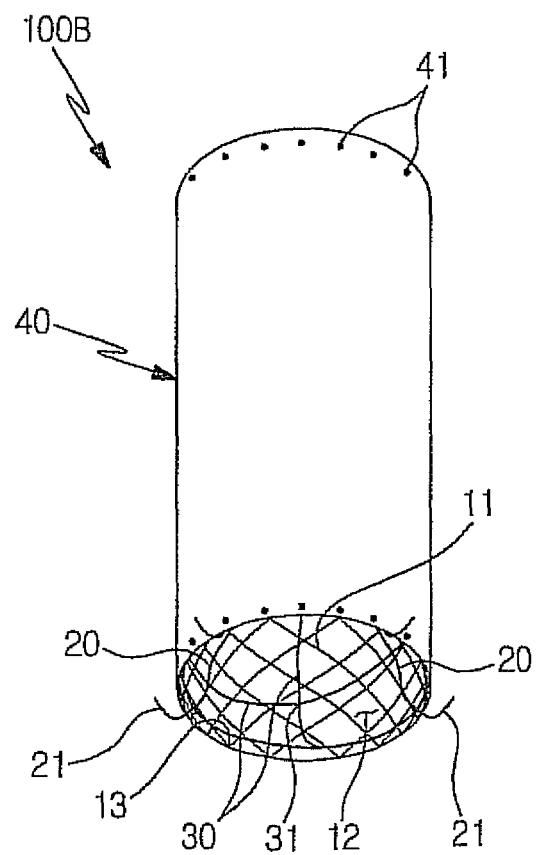
Figure 4A:
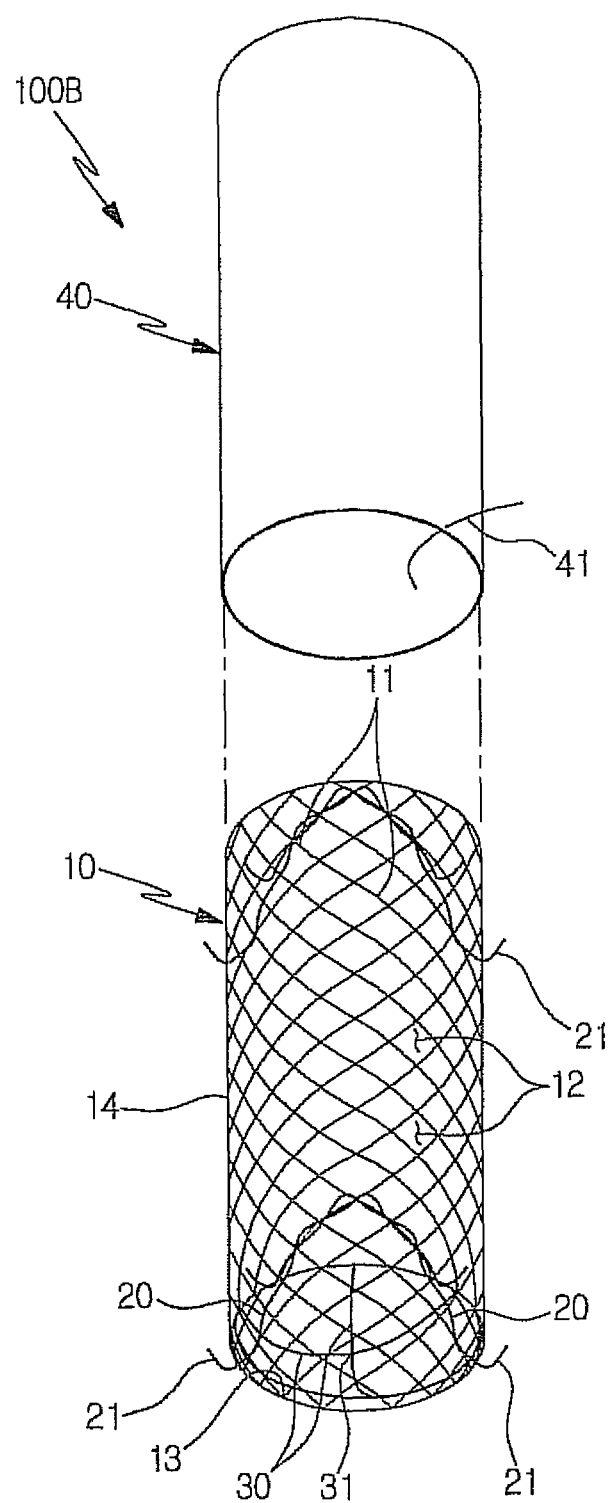
FIGS. 4A and 4B are exploded and assembled perspective views of the stent unit provided with the hooks formed at the upper and lower portions thereof and a membrane, respectively.
Figure 4B:
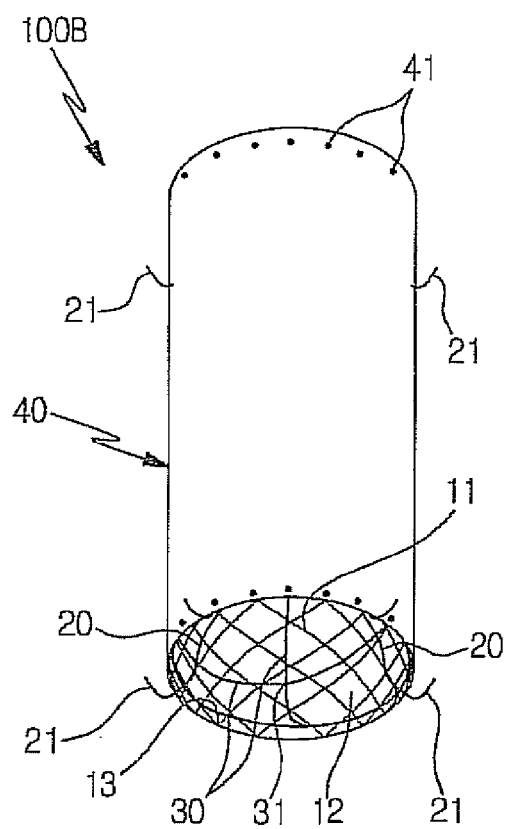
Figure 5A:
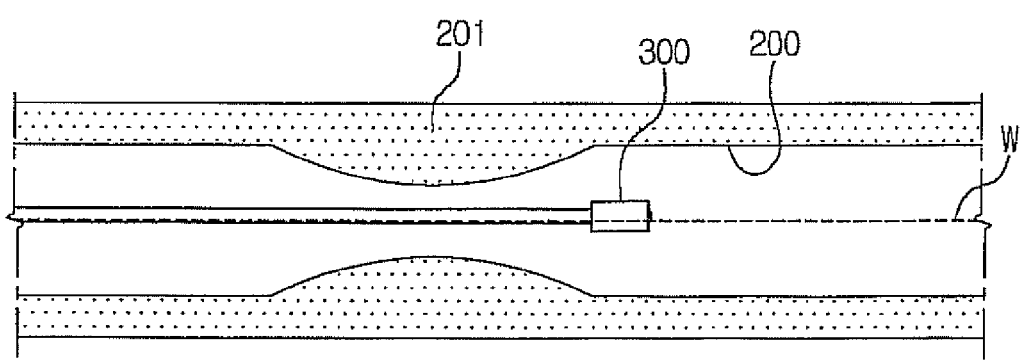
FIGS. 5A to 5C are views illustrating a procedure of a surgical operation of the stent for prostatic urethra expansion using a stent insertion apparatus in accordance with the present invention.
Figure 5B:
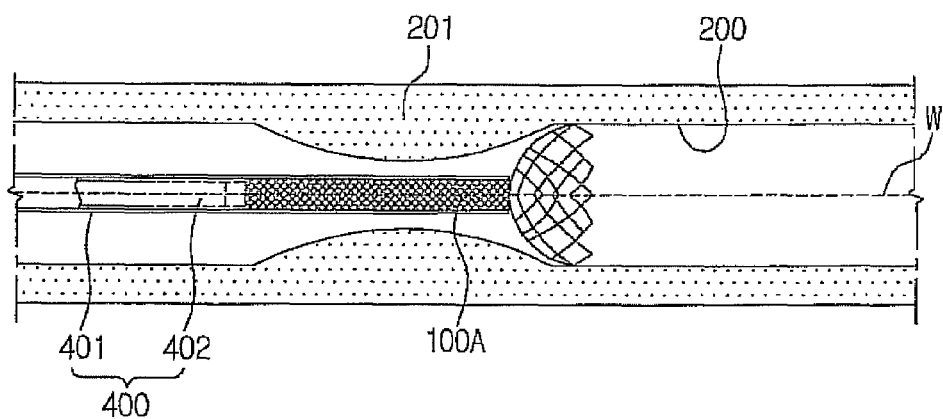
Figure 5C:
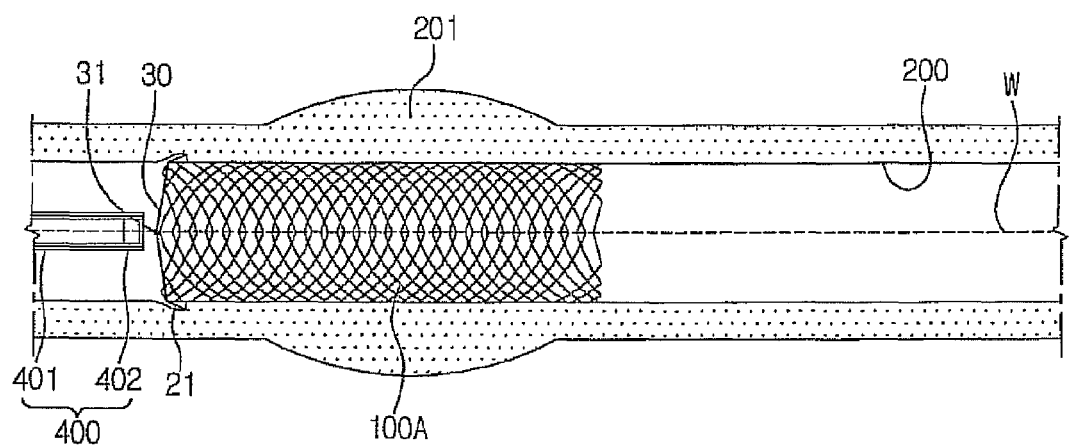
Figure 6A:
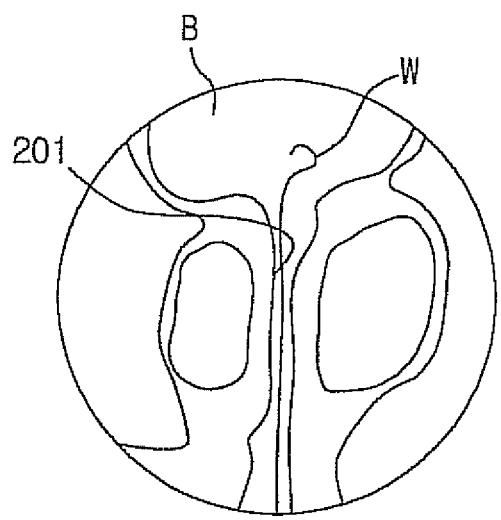
FIGS. 6A to 6D are views illustrating an insertion procedure of the stent for prostatic urethra expansion into a prostatic urethra.
Figure 6B:
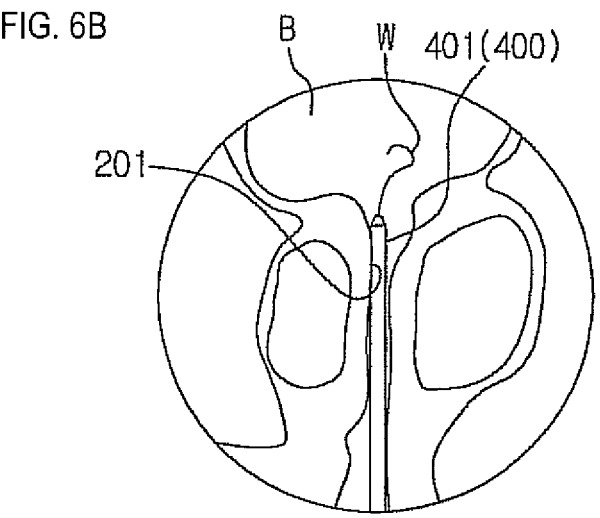
Figure 6C:
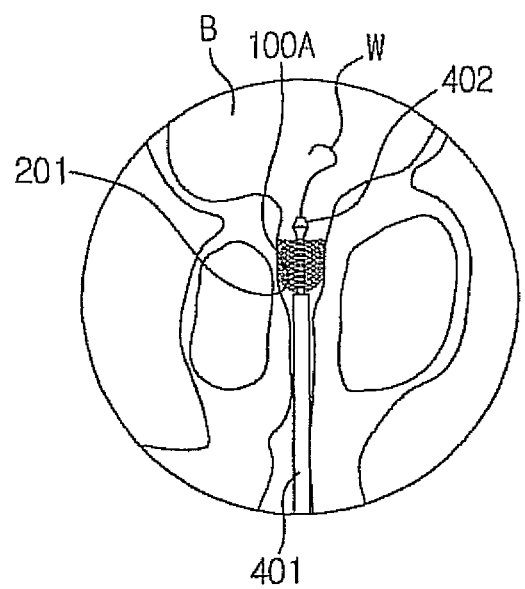
Figure 6D:
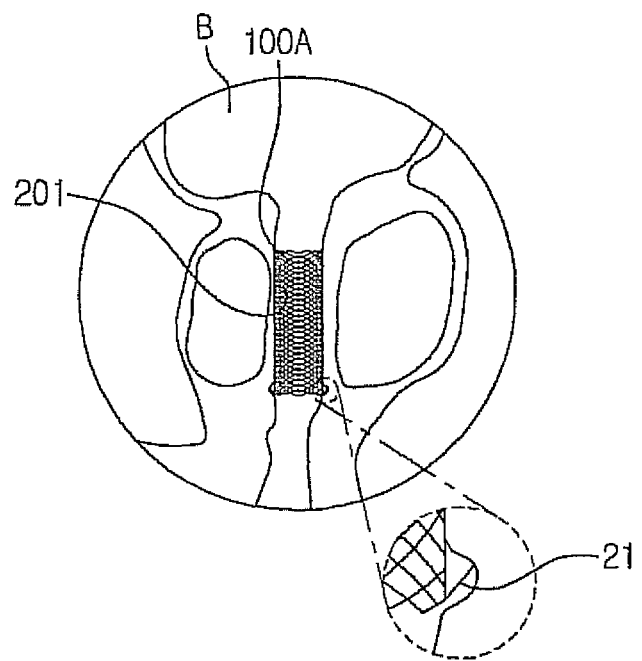
Figure 7A:
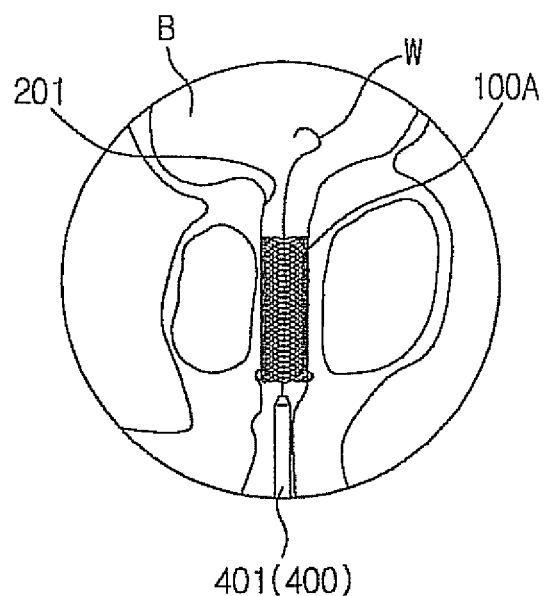
FIGS. 7A to 7D are views illustrating a removal procedure of the stent for prostatic urethra expansion from the prostatic urethra.
Figure 7B:
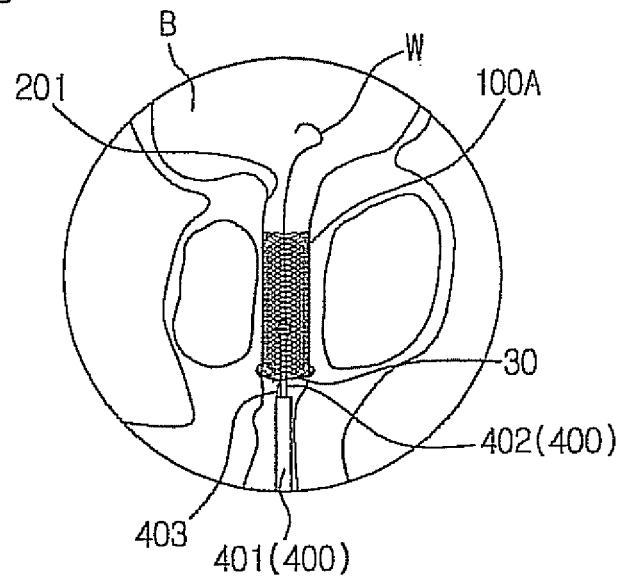
Figure 7C:
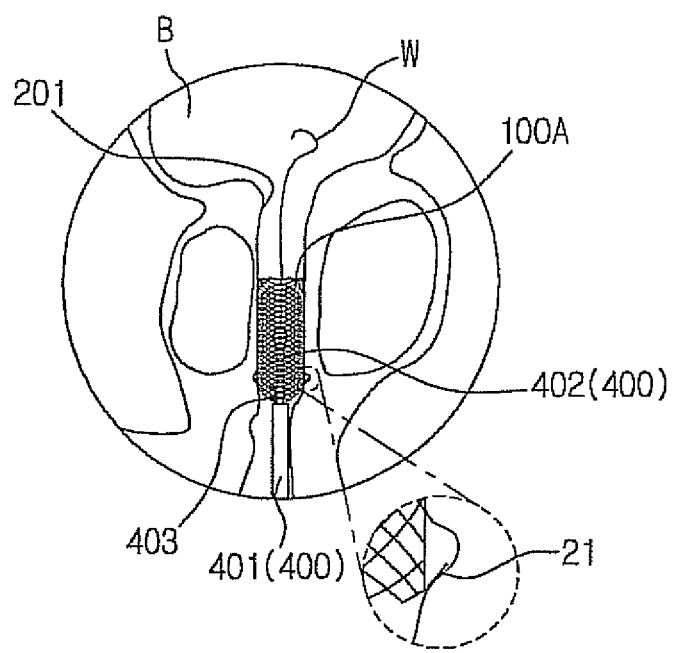
Figure 7D:
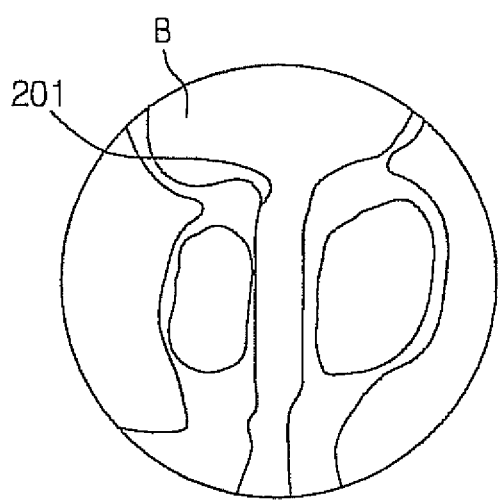

As shown in FIGS. 1 and 2, a stent 100A for prostatic urethra expansion in accordance with one embodiment of the present invention serves to expand and maintain a lumen of an organ of a human body stenosed due to lesion, and a stent unit 10 is formed. The stent unit 10 includes a cylindrical body 14 provided with space parts 12 formed by knotting or crossing, in a zigzag shape, one or more strands of shape memory alloy wires 11, and a plurality of bending terminals 13 formed at both ends of the cylindrical body 14 along the circumference of the cylindrical body 14.

Further, a pair of hook wires 20 passes through the plural space parts 12 located in the lengthwise direction of the cylindrical body 14, and is knotted to the shape memory alloy wires 11 so as to cross each other in a zigzag shape.

Both ends of the hook wires 20 are wound on the bending terminals 13 opposite to each other in the circumferential direction of the cylindrical body 14, and then are bent upwardly to the outside, thereby producing hooks 21.

Here, the hook wires 20 may be made of the same material as the shape memory alloy wires 11.

That is, the hook wires 20 in a pair are knotted together on the inner circumferential surface of the cylindrical body 14 so as to cross each other.

Further, the hook wires 20 may be installed at both ends of the cylindrical body 14 of the stent unit 10 such that the hooks 21 formed at both ends of the cylindrical body 14 face in the same direction.

A pair of hanging strings 30 is arranged perpendicular to one another, such that the hanging strings 30 pass through the space parts 12 of the end of the cylindrical body 14 at which the hooks 21 are formed and are hung onto the bending terminals 13.

The hanging strings 30 are knotted together, thus forming a hanging knot 31 located at the center of the cylindrical body 14.

Here, the hanging knot 31 is located at the center of the cylindrical body 14, and, when the hanging knot 31 is pulled to remove the stent unit 10, the stent unit 10 is extended in the lengthwise direction and the diameter of the stent unit 10 is reduced. Thereby, the stent 100A for prostatic urethra expansion is obtained.

As shown in FIGS. 3A and 3B and FIGS. 4A and 4B, a stent 100B for prostatic urethra expansion in accordance with another embodiment of the present invention serves to expand and maintain a lumen of an organ of a human body stenosed due to lesion, and a stent unit 10 is formed. The stent unit 10 includes a cylindrical body 14 provided with space parts 12 formed by knotting or crossing, in a zigzag shape, one or more strands of shape memory alloy wires 11, and a plurality of bending terminals 13 formed at both ends of the cylindrical body 14 along the circumference of the cylindrical body 14.

Further, a pair of hook wires 20 passes through the plural space parts 12 located in the lengthwise direction of the cylindrical body 14, and is knotted to the shape memory alloy wires 11 so as to cross each other in a zigzag shape.

Both ends of the hook wires 20 are wound on the bending terminals 13 opposite to each other in the circumferential direction of the cylindrical body 14, and then are bent upwardly to the outside, thereby producing hooks 21.

Here, the hook wires 20 may be made of the same material as the shape memory alloy wires 11.

That is, the hook wires 20 in a pair are knotted together on the inner circumferential surface of the cylindrical body 14 so as to cross each other.

Further, the hook wires 20 may be installed at both ends of the cylindrical body 14 of the stent unit 10 such that the hooks 21 formed at both ends of the cylindrical body 14 face in the same direction.

A pair of hanging strings 30 is arranged perpendicular to one another, such that the hanging strings 30 pass through the space parts 12 of the end of the cylindrical body 14 at which the hooks 21 are formed and are hung onto the bending terminals 13.

The hanging strings 30 are knotted together, thus forming a hanging knot 31 located at the center of the cylindrical body 14.

Here, the hanging knot 31 is located at the center of the cylindrical body 14, and, when the hanging knot 31 is pulled to remove the stent unit 10, the stent unit 10 is extended in the lengthwise direction and the diameter of the stent unit 10 is reduced.

Further, a membrane 40 surrounding the outer circumferential surface of the cylindrical body 14 is provided. The cylindrical body 14 is inserted into the cylindrical membrane 40, and then both ends of the cylindrical membrane 40 are fastened to the bending terminals 13 using a fastening string 41.

Here, the membrane 40 is made of a crystalline polymer, such as Poly Tetra Fluoro Ethylene (PTFE). The membrane 40 does not cause erosion and deposition by urine, and prevents luminal tissues of a prostatic urethra from growing into the stent unit 10 through the space parts 12 and then being stenosed to the stent unit 10. Thereby, the stent 100B for prostatic urethra expansion is obtained.

Now, a surgical operation and functions of the stent for prostatic urethra expansion in accordance with the present invention will be described.

As shown in FIGS. 5A to 5C and FIGS. 6A to 6D, the stent 100A or 100B for prostatic urethra expansion is surgically operated using a separate stent insertion apparatus 400 (only the stent 100A for prostatic urethra expansion is illustrated in the drawings).

In order to perform such a surgical operation, a guide wire W together with an endoscope 300 is inserted into a lesion part 201 of a prostatic urethra 200 through a urethra of a patient. When a correct operated position of the stent 100A or 100B for prostatic urethra expansion is obtained through the endoscope 300, the endoscope 300 is removed, and a part of the guide wire W maintains a state exposed to the outside of the patient's body.

Thereafter, under the condition that the stent 100A or 100B for prostatic urethra expansion with a reduced volume is inserted into a fixed tube 401 of the stent insertion apparatus 400, the guide wire W passes through the inside of the front end of the fixed tube 401 and the inside of the front end of a moving tube 402 moving forwards and backwards in the fixed tube 401, thereby enabling the stent insertion apparatus 400 to be inserted into the urethra within a penis of the patient.

Here, the front end of the fixed tube 401 is located in the rear of the lesion part 201 of the prostatic urethra 200, and then the moving tube 402 moves forwards to push the stent 100A or 100B for prostatic urethra expansion out of the fixed tube 401.

The stent 100A or 100B for prostatic urethra expansion, pushed by the moving tube 402 and then exposed, is expanded in volume and restored to its original shape, and thus pushes the prostatic urethra 200 stenosed by the lesion part 201 outwards and expands the lumen of the prostatic urethra 200.

While the stent 100A or 100B for prostatic urethra expansion is expanded in volume and restored to its original shape, the hooks 21 are hung onto the luminal wall of the prostatic urethra 200. Thereby, the stent 100A or 100B for prostatic urethra expansion is not introduced into the bladder B of the patient due to movement of the patient.

Here, the operated position of the stent unit 10 is configured such that the hanging knot 31 is located at the lower part and the hooks 21 face upwards.

After the surgical operation of the stent 100A or 100B for prostatic urethra expansion is completed, the stent insertion apparatus 400 and the guide wire W are removed through the urethra.

Thereby, the stent 100A or 100B for prostatic urethra expansion expands the prostatic urethra 200, thus assisting smooth discharge of urine.

Further, the stent 100B for prostatic urethra expansion enables the membrane 40 to prevent tissues of the luminal wall of the prostatic urethra 200 from coming into direct contact with the stent unit 10 and from growing into the stent unit 10 through the space parts 12 and then being stenosed to the stent unit 10.

As shown in FIGS. 7A to 7D, when the expansion of the lumen of the prostatic urethra 200 or the treatment for the lesion part 201 is completed after the surgical operation of the stent 100A or 100B for prostatic urethra expansion, the stent 100A or 100B for prostatic urethra expansion is removed. In order to remove the stent 100A or 100B for prostatic urethra expansion, the stent insertion apparatus 400 is inserted through the urethra along the guide wire W, under the condition that a separate removal wire 403 in the shape of a hook is inserted into the end of the moving tube 402 of the stent insertion apparatus 400, and is located in front of the hanging knot 31.

Thereafter, when the removal wire 403 is hung on the hanging knot 31 and then is pulled, the stent 100A or 100B for prostatic urethra expansion is pulled by the hanging strings 30 and the volume of the stent 100A or 100B for prostatic urethra expansion is reduced, and thus the stent 100A or 100B for prostatic urethra expansion is inserted into the fixed tube 401 while separating the hooks 21 from the luminal wall. Then, the stent insertion apparatus 400 is removed from the body of the patient. Thereby, the removal operation of the stent 100A or 100B for prostatic urethra expansion is completed.

As apparent from the above description, the present invention provides a stent for prostatic urethra expansion which does not generate stones, does not move to the inside of a bladder, and expands and maintains a lumen of a stenosed prostatic urethra, thereby reducing post-operative recovery time.

Further, a membrane is fastened to the external surface of a stent unit so as to prevent luminal tissues of the prostatic urethra from being stenosed to the stent unit, thereby preventing induction of secondary injury during removal of the stent unit.

Moreover, a hanging direction of the hooks is reverse to a removing direction of the stent unit so as to prevent injury of the stent unit on the lumen of the prostatic urethra during removal of the stent unit, thereby preventing secondary infection.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A stent therefor-configured to expand and maintain a lumen of an organ of a human body stenosed due to a lesion, the stent comprising:
   a stent unit including a cylindrical body, the cylindrical body including:
      space parts formed by knotting or crossing one or more strands of shape memory alloy wire in a zigzag shape, the space parts being arranged in a lengthwise direction of the cylindrical body, and
      a plurality of bending terminals formed at both ends of the cylindrical body, along a circumference of the cylindrical body;
   a first pair of hook wires passing through the space parts at one end of the cylindrical body, where opposite ends of each hook wire, of the pair of hook wires, are wound on respective ones of the plurality of bending terminals positioned opposite to one another in a circumferential direction of the cylindrical body, and where each of the ends of each hook wire, of the pair of hook wires, is bent to produce first hooks therefor-configured to engage an inner wall of the lumen of the organ; and
   a pair of hanging strings arranged perpendicular to one another, such that the pair of hanging strings passes through space parts at one end of the cylindrical body, the pair of hanging strings are attached to the bending terminals, and the pair of hanging strings is knotted together so as to form a hanging knot, located at a center of the cylindrical body, which reduces a volume of the cylindrical body when pulled and causes the first hooks to disengage from the inner wall of the lumen when the volume of the stent is reduced in response to the pulling.

2. The stent according to claim 1, further comprising:
   a second pair of the hook wires passing through space parts at another end of the cylindrical body to form second hooks, where the first hooks and the second hooks are oriented in a same direction.

3. A stent comprising:
   a stent unit including a cylindrical body, the cylindrical body including:
      space parts formed by interweaving one or more strands of shape memory alloy wire, the space parts being arranged in a lengthwise direction of the cylindrical body, and
      a plurality of bending terminals formed at both ends of the cylindrical body along a circumference of the cylindrical body;
   a first pair of hook wires passing through the space parts at one end of the cylindrical body, where opposite ends of each hook wire, of the plurality of hook wires, are attached to respective ones of the plurality of bending terminals positioned opposite to one another in a circumferential direction of the cylindrical body, and where each of the ends of each hook wire, of the pair of hook wires, is bent to produce first hooks therefor-configured to engage a lumen of an organ;
   a pair of hanging strings arranged perpendicular to one another, such that the pair of hanging strings passes through space parts at one end of the cylindrical body, the pair of hanging strings are attached to the bending terminals, and the pair of hanging strings is knotted together so as to form a hanging knot, located at a center of the cylindrical body, which reduces a volume of the cylindrical body when pulled and causes the first hooks to disengage from the lumen when the volume of the stent is reduced in response to the pulling; and
   a membrane, formed in a cylindrical shape, to surround an outer circumferential surface of the cylindrical body, both ends of the cylindrical membrane being fastened to the plurality of bending terminals using a fastening string.

4. The stent according to claim 3, further comprising:
   a second pair of the hook wires passing through space parts at another end of the cylindrical body to form second hooks, where the first hooks and the second hooks are oriented in a same direction.

5. The stent according to claim 3, where the first hook wires and the second hook wires are formed of the same material as the shape memory alloy wires.

6. The stent according to claim 2, where the hanging knot causes the second hooks to disengage from the inner wall of the lumen when the volume of the stent is reduced in response to the pulling of the hanging knot.

7. The stent according to claim 4, where the hanging knot causes the second hooks to disengage from the lumen when the volume of the stent is reduced in response to the pulling of the hanging knot.

* * * * *